(12) United States Patent
de Mooy

(10) Patent No.: US 7,076,821 B2
(45) Date of Patent: Jul. 18, 2006

(54) MODULAR PATIENT SUPPORT SYSTEM FOR USE IN RADIOTHERAPY TREATMENTS

(75) Inventor: Leendert Gerrit de Mooy, Gouda (NL)

(73) Assignee: Sinmed B.V., Reeuwijk (NL)

( * ) Notice: Subject to any disclaimer, the term of this patent is extended or adjusted under 35 U.S.C. 154(b) by 50 days.

(21) Appl. No.: 10/894,896

(22) Filed: Jul. 20, 2004

(65) Prior Publication Data

US 2005/0028279 A1 Feb. 10, 2005

(30) Foreign Application Priority Data

Aug. 7, 2003 (NL) .................................. 1024063

(51) Int. Cl.
*A61G 13/12* (2006.01)
*A61G 13/00* (2006.01)
(52) U.S. Cl. ............................................. 5/601; 5/621
(58) Field of Classification Search .................... 5/601, 5/600, 621–624, 632, 640, 646, 648, 658; 378/177, 208, 209
See application file for complete search history.

(56) References Cited

U.S. PATENT DOCUMENTS

| | | | |
|---|---|---|---|
| 4,688,780 A | 8/1987 | Hanz | |
| 5,276,927 A * | 1/1994 | Day | 5/622 |
| 5,560,728 A * | 10/1996 | McFadden | 403/53 |
| 5,632,275 A | 5/1997 | Browne et al. | |
| 5,661,859 A * | 9/1997 | Schaefer | 5/621 |
| 5,675,851 A | 10/1997 | Feathers | |
| 6,003,174 A | 12/1999 | Kantrowitz et al. | |
| 6,199,233 B1 * | 3/2001 | Kantrowitz et al. | 5/601 |
| 6,557,195 B1 * | 5/2003 | Dinkler | 5/601 |
| 6,584,630 B1 * | 7/2003 | Dinkler | 5/622 |
| 6,813,788 B1 * | 11/2004 | Dinkler et al. | 5/622 |
| 2005/0028279 A1 * | 2/2005 | de Mooy | 5/601 |

FOREIGN PATENT DOCUMENTS

DE 20117596 U1 3/2002

* cited by examiner

*Primary Examiner*—Robert G. Santos
(74) *Attorney, Agent, or Firm*—Ladas and Parry LLP

(57) ABSTRACT

The invention relates to a modular patient support system for use with radiotherapy treatments comprising a basic portion to be fixedly mounted and an exchangeable radiotransparent modular portion, said portion to be fixedly mounted being provided with a radiotransparent supporting part intended for supporting an exchangeable modular portion and means being provided for exactly positioning said modular portion in relation to said basic portion and coupling it to said basic portion.

18 Claims, 5 Drawing Sheets

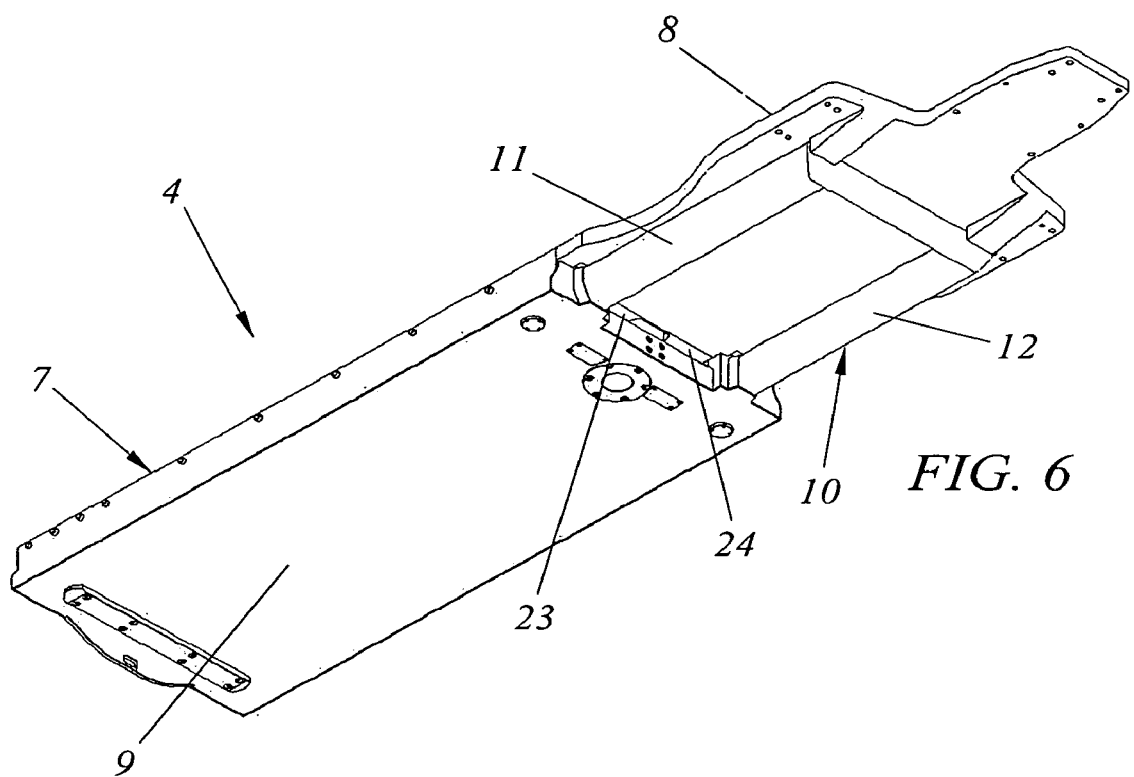
FIG. 6
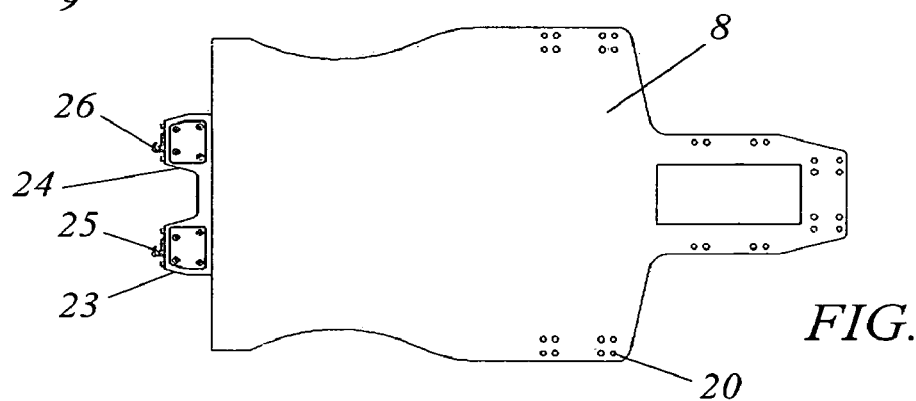
FIG. 7A
FIG. 7B
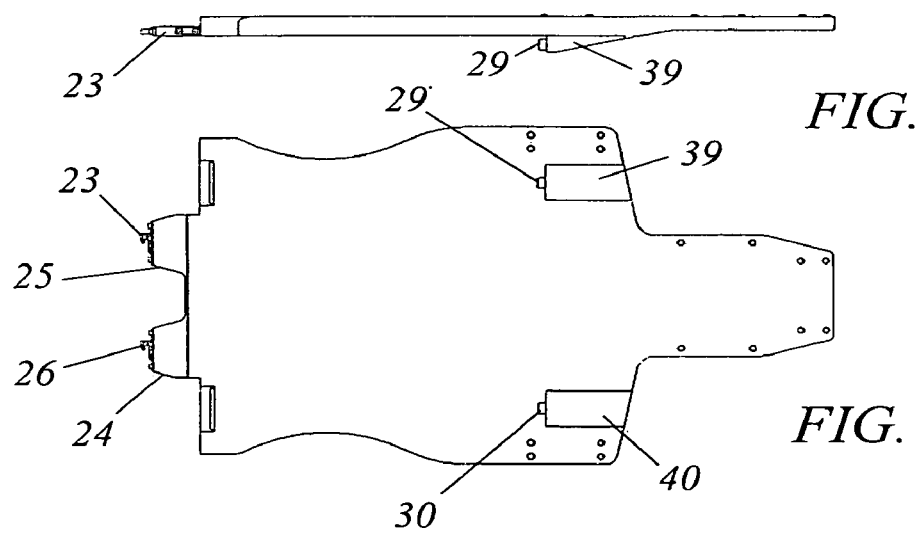
FIG. 7C

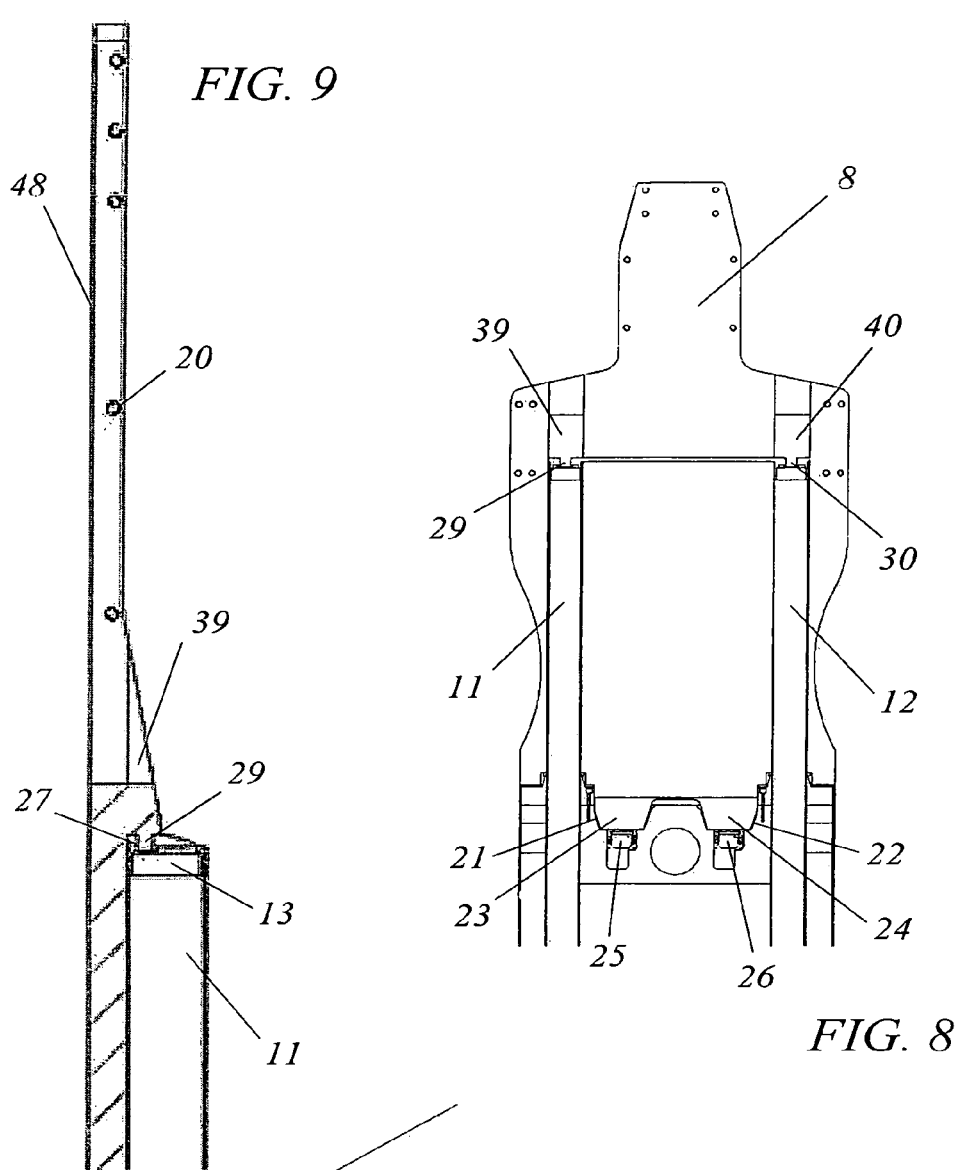
FIG. 9
FIG. 8
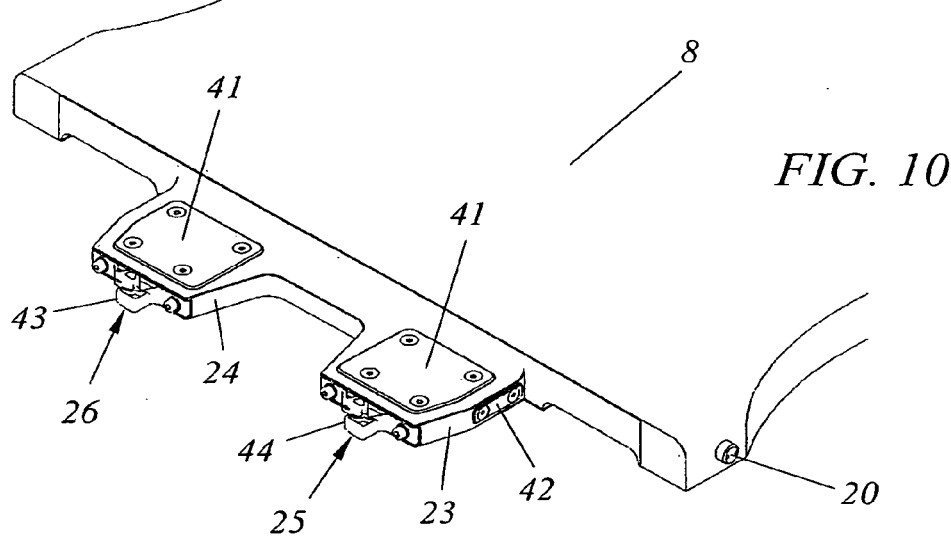
FIG. 10

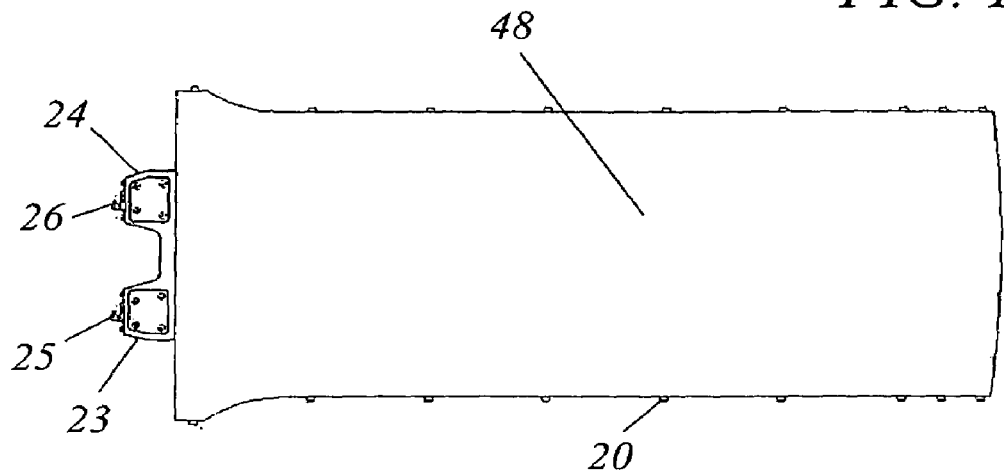
FIG. 11A
FIG. 11B
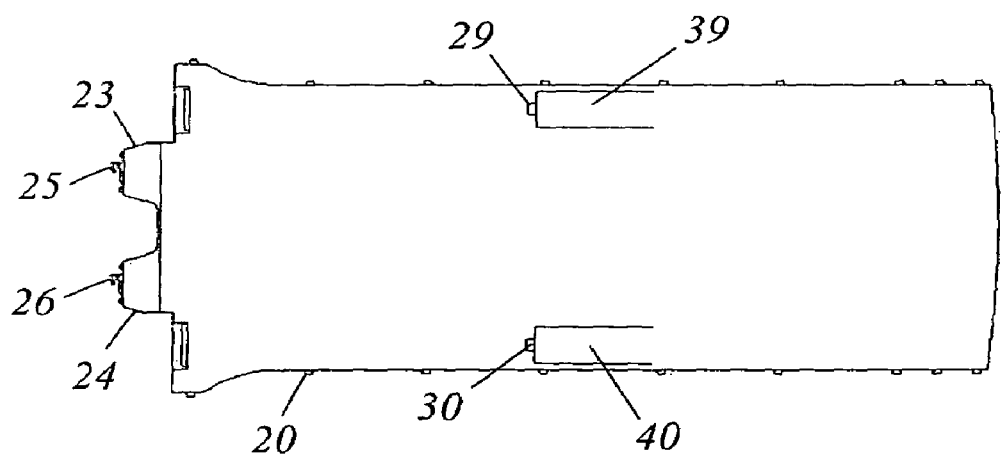
FIG. 11C

MODULAR PATIENT SUPPORT SYSTEM FOR USE IN RADIOTHERAPY TREATMENTS

FIELD OF THE INVENTION

The present invention relates to a modular patient support system for use in radiotherapy treatments, at least comprising a radiotransparent structure.

BACKGROUND OF THE INVENTION

Such patient supports are known in various embodiments and are substantially intended for being mounted on adjustable tables belonging to an arrangement with irradiation aparatus. With a patient support intended for radiotherapy treatments, rigidity and radiotransparency of said support is of great importance. In all current patient supports, at least a part of the structure comprises metal parts providing rigidity and/or fixation possibilities of accessories. These metal parts cause scatter of the radiation beam. Therefore, with the current patient supports it should always be possible to irradiate past the metal parts. Due to this, it is not possible to irradiate a patient across any desired angle. Further, current supports are often wide, for the purpose of being able to perform all treatments on one patient support and to have enough space to be able to irradiate past said metal parts. This width of the support hinders the number of degrees of freedom of the irradiating member.

SUMMARY OF THE INVENTION

The object of the invention is to provide a modular patient support system having exchangeable modular parts, projecting freely, being sufficiently rigid and fully radiotransparent. A further object is to provide an adapted modular part for each specific treatment.

Accordingly, the invention provides for that the patient support system comprises a basic portion to be mounted fixedly and an exchangeable radiotransparent modular portion, said basic portion to be mounted fixedly being provided with a radiotransparent supporting part for supporting an exchangeable modular part and means being provided for positioning said modular portion in relation to the basic portion and for coupling it to said basic portion. The basic portion is intended for being fixedly mounted onto an adjustable table belonging to irradiation equipment and therefore need not have any special radiotransparent properties. The supporting portion projecting from said basic portion projects out of the basic portion from approximately the table edge and will be situated completely or partly within the range of the irradiation equipment. The modular portion to be situated onto the supporting portion is a sandwich structure made of the materials commonly used for it, such as for example layers of oriented fibres, e.g. carbon fibres, said fibres being embedded in an epoxy resin, and a foam material or a honeycomb structure.

Apart from the advantage of a completely radiotransparent support, the modular system according to the invention has the further advantages that with the radiotransparent supporting portion, the modular portion can be made smaller than is usual with said known patient supports. With the known structures, the metal reinforcements must be kept outside the range to be irradiated, therefore outside of the body contour of the patients to be treated. The advantages of a less wide support are, among other things, that the irradiating member can be brought closer to the tumors to be treated and that the entity of fixed basic portion and modular portion can be positioned within a larger range in relation to said radiating member. With the known supports, the positioning range is limited because of the dimensions of said entity. Therefore, the radiating member will easily abut the support or the support will easily abut the stationary parts of the irradiation device.

A further advantage is that the specific modular portions can be made for irradiating tumors in specific target areas, to which end the modular portions can be adapted in shape. The modular patient support can be made narrower than usual, as a result of which more adjusting possibilities are provided. This also enables a more effective irradiation and conservation of a greater amount of healthy tissue. Since the modular portions are intended for a certain target area, they can be provided with speciale fixing positions for accessories to be used.

Preceding the actual irradiation, the patient mostly passes through the CT scanning device, where the tumor(s) is/will be located. Using this information, an irradiation planning is made. A great advantage is achieved by providing the CT scanner with a patient support which corresponds to the patient support according to the invention as far as positioning of the patient, dosimetric properties and markers are concerned. The previously required calculating operations of the CT support to the form and dosimetric properties of the patient support in the irradiating device can be omitted. This makes planning the irradiation much quicker, more effective and reliable and positioning of the patient is much more accurate and better reproducible. This again leads to a more accurate and more effective irradiation of the tumor.

According to a further development it is provided for that the radiotransparent supporting portion of said fixed basic portion substantially comprises spaced-apart arms extending in longitudinal direction of said basic portion, having their ends connected to one another by a connecting part. Here, the arms of said radiotransparent supporting portion comprise tubular sleeves, their lower and upper sides comprising a hybrid structure of one directional carbon fibres and cross-woven carbon fibres. The one-directional carbon fibres preferably have a great stiffness and further, the carbon fibres are embedded in epoxy resin. At least one side of the tubular sleeve has across a part of its length a sandwich structure having a core of foam material and at both sides a layer of carbon fibres. More in particular, this layer comprises cross-woven carbon fibre embedded in epoxy resin. This structure of the supporting profiles is a weighted optimization between strength and stiffness requirements and the dosimetric requirements.

The dosimetric properties are especially important at the sides, since they cover a much larger rotational angle of the irradiation member than the bottom and top sides of the tubular sleeves per se do. The dosimetric properties directly depend on the specific density and the properties of the material passed by the radiation. By the specific construction of the profiles it is achieved that the beam of radiation is weakened as little as possible and an effect of accumulation of radiation on the skin is minimized, while the strength and stiffness of said profiles remains guaranteed.

According to a yet further development, it is provided that the tubular sleeves, seen in cross-section, become narrower from the upwardly situated plane of contact with a modular part downwards. A preferred embodiment provides for, that the tubular sleeves have an obliquely extending plane at the outwardly facing sides. Thus, the stiffness and strength of the supporting arms can remain guaranteed, while a larger degree of free movement of the radiation member enhances its number of adjusting possibilities.

In the modular system according to the invention it is important that the modular portion and the fixed basic portion can be properly positioned and secured in relation to one another. To that end, the modular portion and the fixed basic portion are provided with positioning means and means for having the modular portion engage the fixed basic portion with a snap connection.

According to a first development, first positioning means are provided, comprising one or more slides mounted on the extreme end of a modular portion and holes corresponding to them for receiving the pins in the extreme end of the fixed basic portion. In order to achieve an exact positioning as well as a proper fit of the slides in the holes, it is further provided for, that the slides have adjusting means for being able to set a modular portion in a desired position in relation to the fixed basic portion.

In order to establish an accurate positioning which will be exactly reproduced again on renewed placement of a modular portion, it is necessary to mount positioning means in the radiotransparent portion of the support as well. According to a further development, to that end, second positioning means are provided, comprising one or more pins mounted on a modular portion, said pins being made of a radiotransparent material, and corresponding holes for receiving the pins in the radiotransparent supporting portion of the fixed basic portion. These second positioning means prevent the modular portion from moving in the remaining level of freedom, therefore in vertical direction, and also serve for transmit the forces exerted on the modular portion to the supporting portion, as a result of which said first positioning means are relieved from force.

The pins preferably form a whole with the modular portion. The holes for receiving the pins are preferably in the form of bushes mounted in the connecting part through which the extreme ends of the tubular sleeves are connected to one another, in which said bushes can extend into the tubular sleeves. The respective bushes can be a whole with the connecting part and a tubular sleeve.

Further, according to the invention it is provided for that one or more snap connection members are applied between modular portion and fixed basic portion. The part of said snap connection members on the modular portion are preferably mounted on the extreme ends of the pins of first positioning means. In this way, when assembling basic portion and modular portion, said snap connection members will be situated in the basic portion completely and thus the snap connection members need not be radiotransparent.

BRIEF DESCRIPTION OF THE DRAWINGS

The invention is further explained by way of the example illustrated in the drawing, in which:

FIG. 6 shows a perspective bottom view of the basic portion and a modular portion coupled to it;

FIGS. 7A,B,C show three views of a module intended for treating the areas of head and neck;

FIG. 8 shows a bottom view of the basic portion and a module coupled to it, intended for treating the areas of head and neck;

FIG. 9 shows a cross-section of the basic portion and a module coupled to it, intended for treating the areas of thorax and pelvis;

FIG. 10 shows a perspective view of the part of the snap connection members mounted on a modular portion; and FIGS. 11A,B,C show three views of a module intended for treating the areas of thorax and pelvis.

DETAILED DESCRIPTION

Figure 1:
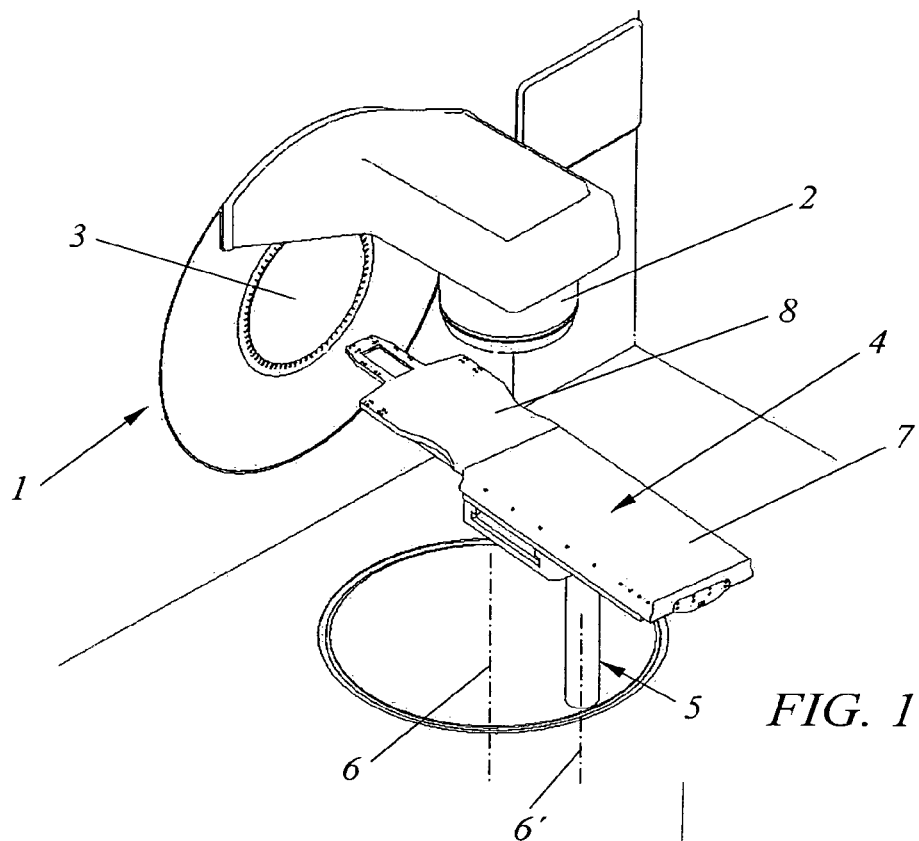
FIG. 1 shows a perspective view of an irradiation device having a fixed basic portion mounted on an adjustable table and a modular portion coupled to it.
Figure 2:
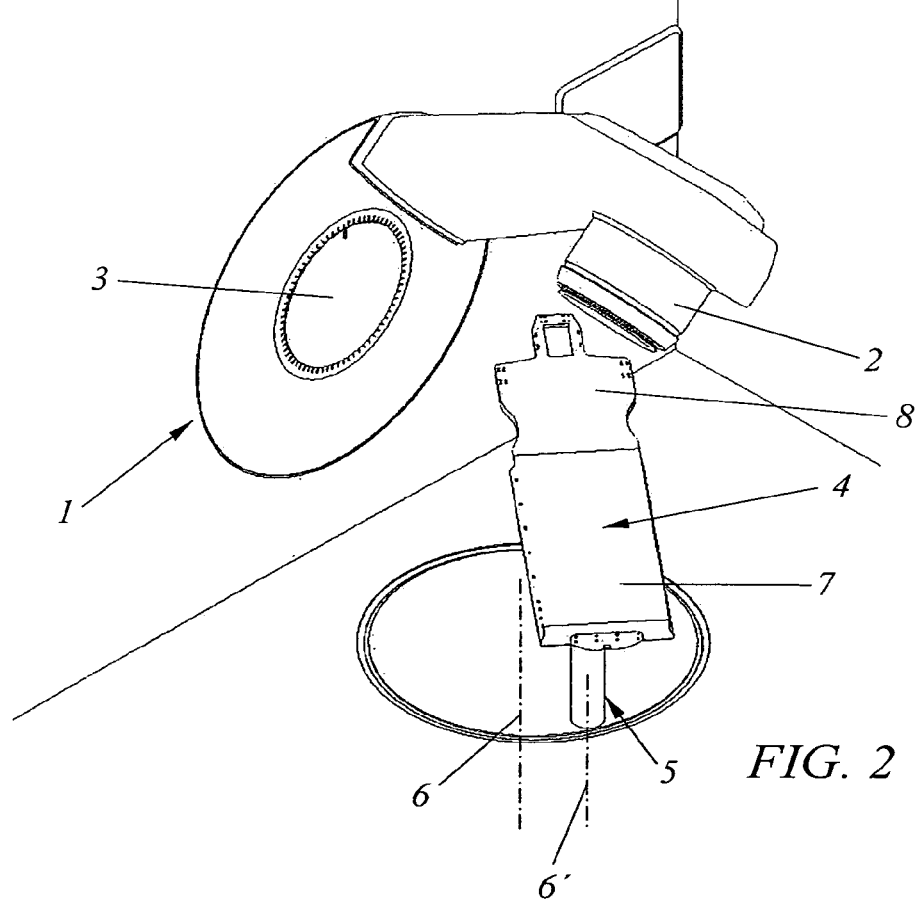
FIG. 2 shows the arrangement of FIG. 1 in another position.

FIGS. 1, 2 show schematically an arrangement of an irradiation device 1 having an radiating member 2 that can be rotated around a horizontal shaft 3. In this way, the radiating member can be brought into any position in relation to a patient to be irradiated within a range of 360° and therefore in any series of subsequent positions.

A patient to be treated is supported by a support 4. The support 4 is mounted on an adjustable table 5, which is rotatable around two vertical axes 6, 6' and is adjustable in height and in which the adjustable table 5 can move the support 4 horizontally and laterally. In this way, the tumor to be treated of a patient can be positioned exactly in the radiation center of radiating member 2. The support 4 comprises a basic portion 7 fixedly applied on the table 5 and a modular portion 8 coupled to said basic portion.

Figure 3:
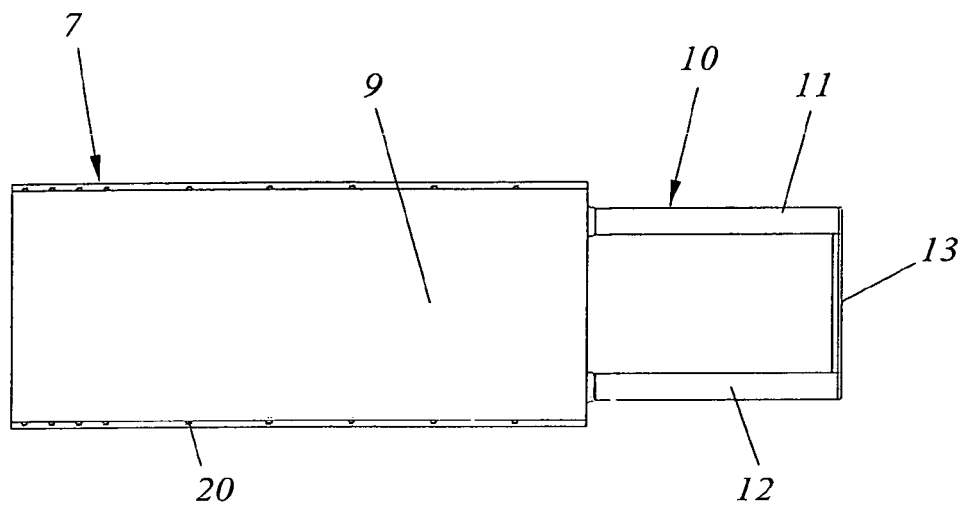
FIG. 3 shows a plan view of the basic portion.
Figure 4:
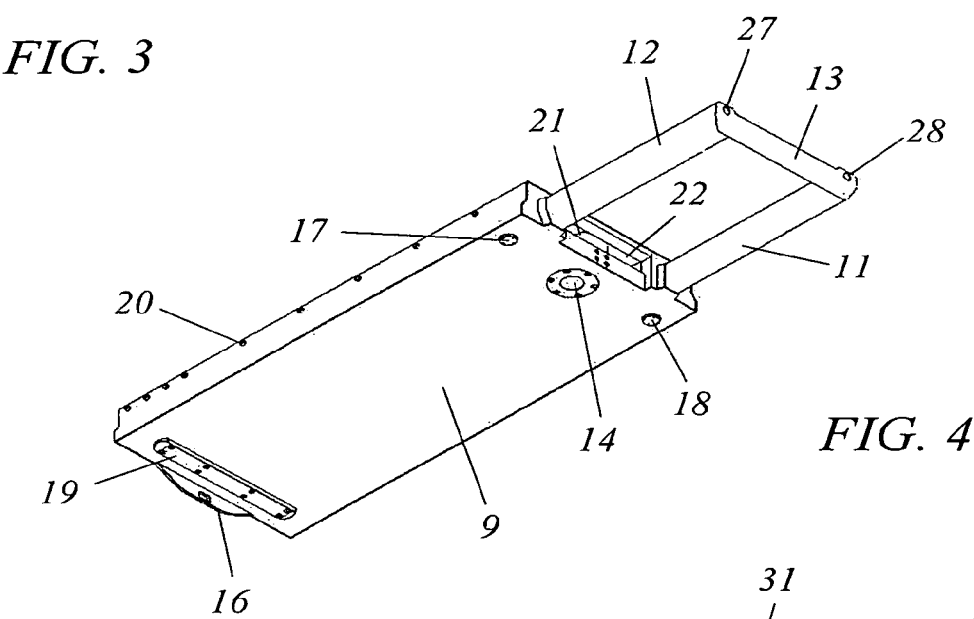
FIG. 4 shows a perspective bottom view of the basic portion.

FIGS. 3, 4 show respectively a plan view and a perspective bottom view of said basic portion 7 of support 4. The basic portion comprises a flat plate 9 and a supporting part 10 projecting from it, which is intended for supporting modular portions 8. Supporting part 10 is comprised of radiotransparent supporting arms 11, 12 having their extreme ends connected through a likewise radiotransparent connecting piece 13.

Plate 9 has its bottom side provided with means for attachment to an adjustable table 5 belonging to an irradiation device 1. In the given example, the means comprise a hole 14 for receiving a pin not further illustrated in the drawing, on the adjustable table 5, mounting profile 16 at the rear end and adjusting plates 17, 18, 19 for aligning said plate 9. At the sides of the plate 9 fixing cams 20 have been mounted for securing auxiliary means.

At the extreme end of plate 9, situated between the supporting arms 11, 12 are openings 21, 22 for receiving first positioning elements, slides 23, 24 at the extreme end of a modular portion 8. Said openings 21, 22 also contain the complementary parts of said snap connection members 25, 26 (see FIG. 7) mounted at the extreme ends of respective first positioning elements 23, 24.

In connecting piece 13 at the level of the supporting arms 11, 12 holes 27, 28 for receiving second positioning means, pens 29, 30 (see FIG. 7), situated at the bottom side of a modular portion 8.

Figure 5:
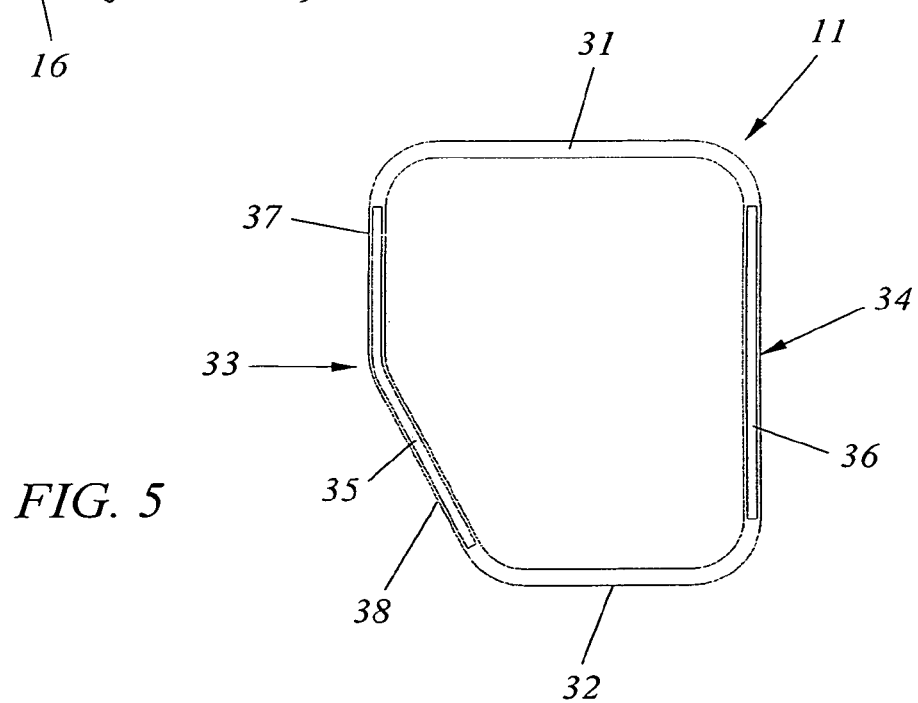
FIG. 5 shows a cross-section of a supporting arm of said basic portion.

FIG. 5 shows a cross-section of a supporting arm 11, 12. The top and bottom sides 31, 32 substantially comprise a hybrid structure having a number of fibre layers, such as carbon fibre layers, for example. In subsequent layers, the carbon fibres can be oriented in substantially one direction, the longitudinal direction or the fibres can be woven in a crossed relation. The sides 33, 34 comprise a sandwich structure having fibre layers, e.g. layers of cross-woven carbon fibres, having a core of a foam material 35, 36. This structure is strong enough to minimize bending of the supporting arms 11, 12. Likewise of great importance is the fact that on account of the small mass of sides 33, 34 of supporting arms 11, 12 weakening and scattering of the radiation is also kept to a minimum to with in such a way that the maximum of radiation will still be situated beyond the skin surface of a patient to be treated.

The outside 33 has a portion 37 extending straight and an angled portion 38, as a result of which the radiation member can be led closer along the patient support.

FIG. 6 shows an assembly of the basic portion 7 with plate 9 and supporting portion 10 and a modular portion 8. Said modular portion 8 is identical to the modular portion shown in FIG. 7 and is especially intended for treating the area of head and neck. Modular portion 8 has its positioning elements, the slides 23, 24 projecting into the openings 21, 22 (see also FIG. 8) and positioning pins 29, 30 into the holes 27, 28. The complementary parts of the snap connection members 25, 26 are engaging. The snap connecting members are preferably of the type in which bringing the parts in and out of engagement occurs by applying a force which is greater than a predetermined threshold value. Due to this, a module is easily mountable and removable.

FIGS. 6, 7 show that positioning pins 29, 30 are oriented in parallel to the lower surface of modular portion 8 and are connected to it through adapters 39, 40. Pins 29, 30, adapters 39, 40 and the modular portion 8 are an entity which is also radiotransparent in its entirety. Modular portion 8 is provided with fixation points 20 for accessories for positioning and fixating the head-neck area.

FIG. 9 shows a cross-section through a supporting arm 11 and a modular portion 48. Modular portion 48 is specially intended for treating tumors in the thorax or pelvic area and is clearly longer than the modular portion meant for treatments in the head-neck areas. At the sides of modular portion 48, fixation cams 20 have been mounted for accessories intended for positioning the pelvic or thorax area. In various practical tests with this longer modular portion, bending at the free extreme end with a 70 kg load at the extreme end proves to be 1 cm maximum. In case of a normal, much smaller load at the extreme end, the degree of bending is much smaller and in the area where the treatment takes place, close to basic portion 7, the degree of bending is well within the margin for being able to perform an accurate treatment.

FIG. 11 provides three views of long modular portion 48. The system with a basic portion 7 having a radiotransparent supporting part 10 protruding from it, combined with the longer modular portion 48, makes it possible that the pelvic region can be treated without having to rotate the table 5 and the entire support 4 across 180°, as is necessary with most of the known systems.

FIG. 10 shows the first positioning elements, the slides 23, 24, in more detail. The top side and at least one side mounts adjusting plates 41, 42 by which an exact adjustment in horizontal and vertical direction, respectively, is possible as well as an exact fit in the openings 21, 22. The extreme ends of the slides 23, 24 mount hooks 43, 44 being part of snap connection members 25, 26 known per se. The complementary portions are spring-loaded and are designed to enclose the hooks 43, 44 on inserting modular portion 8. It is important that by this, an exact positioning of the fixed basic portion 7 and a modular portion in relation to one another can be effected, which will not show any deviations even with frequent use.

The modular system according to the invention having a fixed basic portion and a modular portion to be coupled to it is extremely well suitable for developing further modular portions for specific purposes. Thus, very specific adaptations come within reach, which can not be realized with the existing patient supports for technical or economical reasons.

What is claimed is:

1. Modular patient support system having a radiotransparent structure for use in radiotherapy treatments, the system comprising a basic portion to be mounted fixedly and an exchangeable radiotransparent modular portion, said basic portion to be mounted fixedly being provided with a radiotransparent supporting part for supporting the exchangeable modular portion and means for positioning said modular portion in relation to the basic portion and for coupling it to said basic portion to be fixedly mounted, wherein the modular portion and the basic portion are provided with positioning means and means for having said modular portion engage said fixed basic portion by a snap connection.

2. Modular system according to claim 1, characterized in that the radiotransparent supporting part of the fixed basic portion substantially comprises spaced-apart arms extending in longitudinal direction of said basic portion having its extreme ends connected to one another through a connecting part.

3. Modular system according to claim 2, characterized in that the arms of the radiotransparent supporting part substantially consist of tubular sleeves with bottom and top sides thereof comprising a hybrid structure having one directional carbon fibres and cross-woven carbon fibres and at least one side having across at least a part of its length a core of foam material with a layer of cross-woven carbon fibres on each side of the core of foam material.

4. Modular patient support system having a radiotransparent structure for use in radiotherapy treatments, said system comprising a fixed basic portion, an exchangeable radiotransparent supporting element for supporting a patient and means for positioning said supporting element in respect to said basic portion, said basic portion comprising spaced apart arms extending in a longitudinal direction thereof for supporting a part of said exchangeable radiotransparent supporting element, said arms having extreme ends that are connected to one another by a connecting element, said arms comprising tubular sleeves with bottom and top sides thereof comprising a hybrid structure having uni-directional carbon fibers and cross-woven carbon fibers and at least one side having across at least a part of its length a core of foam material with a layer of cross-woven carbon fibers on each side of the core of foam material, and means for removably and fixedly connecting said support element to said basic portion.

5. Modular system according to claim 4, wherein the tubular sleeves, seen in cross-section, become narrower from the upwardly situated plane of contact with the supporting element downwards.

6. Modular system according to claim 5, characterized in that the tubular sleeves have an obliquely extending plane at the outwardly facing sides.

7. Modular system according to claim 6, characterized in that the connecting part by which the extreme ends of the tubular sleeves are connected to one another substantially comprises a structure having carbon fibres and constitutes an entity with the tubular sleeves.

8. Modular system according to claim 7, characterized in that the connecting part, seen in cross-section, has a vertical size which is many times greater than the thickness of the connecting part.

9. Modular system according to claim 4, wherein the supporting element and the basic portion are provided with positioning means and means for having said supporting element engage said fixed basic portion by a snap connection.

10. Modular system according to claim 9, characterized in that the first positioning means comprise one or more slides mounted on an extreme end of the supporting element and openings corresponding for receiving pins in an extreme end of the fixed basic portion.

11. Modular system according to claim 10, characterized in that the slides are provided with setting means for setting the support element in a desired position in relation to the fixed basic portion.

12. Modular system according to claim 9, characterized in that second positioning means comprise one or more pins mounted on the supporting element, said pins being made of a radiotransparent material, and holes for receiving the pins in said fixed basic portion.

13. Modular system according to claim 12, characterized in that the pins constitute an entity with the supporting element.

14. Modular system according to claim 12, characterized in that the holes for receiving the pins are constituted by bushings mounted in the connecting part, by which the extreme ends of the tubular sleeves are connected to one another, said bushings continuing into the tubular sleeves.

15. Modular system according to claim 14, characterized in that each bushing constitutes an entity with the connecting part and a tubular sleeve.

16. Modular system according to claim 9, characterized in that one or more snap connection members are provided between the modular portion and the fixed basic portion.

17. Modular system according to claim 16, characterized in that the snap connection members are mounted on the extreme ends of the slides of said first positioning means.

18. Modular system according to claim 4, characterized in that the fixed basic portion is provided with positioning means for positioning the fixed basic portion on an adjustable table.

* * * * *